US009833529B2

(12) United States Patent
Tipton et al.

(10) Patent No.: US 9,833,529 B2
(45) Date of Patent: Dec. 5, 2017

(54) STERILIZATION CASSETTE SYSTEMS, INSTRUMENT RETENTION SYSTEMS FOR A USE WITH A STERILIZATION CASSETTE, AND CONFIGURABLE INSTRUMENT RETENTION MEMBERS FOR USE THEREWITH

(71) Applicant: HU-FRIEDY MFG. CO., LLC, Chicago, IL (US)

(72) Inventors: David W. Tipton, Chicago, IL (US); Timothy J. Fischer, Chicago, IL (US); David K. Platt, Mount Prospect, IL (US); Chantel D. Willis, Munster, IN (US); Jennifer Radovich Naylor, Batavia, IL (US); Marjavis J. Matthis, Chicago, IL (US); Mark Kurth, Beverly Shores, IN (US); Timothy Payne, Chicago, IL (US); Philip Anthony, Chicago, IL (US)

(73) Assignee: HU-FRIEDY MFG. CO., LLC, Chicago, IL (US)

( * ) Notice: Subject to any disclaimer, the term of this patent is extended or adjusted under 35 U.S.C. 154(b) by 361 days.

(21) Appl. No.: 14/407,521

(22) PCT Filed: Jun. 25, 2013

(86) PCT No.: PCT/US2013/047606
§ 371 (c)(1),
(2) Date: Dec. 12, 2014

(87) PCT Pub. No.: WO2014/004500
PCT Pub. Date: Jan. 3, 2014

(65) Prior Publication Data
US 2015/0151017 A1 Jun. 4, 2015

Related U.S. Application Data

(60) Provisional application No. 61/664,383, filed on Jun. 26, 2012, provisional application No. 61/811,965, filed on Apr. 15, 2013.

(51) Int. Cl.
*A61L 2/26* (2006.01)
*A61B 50/34* (2016.01)
(Continued)

(52) U.S. Cl.
CPC ............. *A61L 2/26* (2013.01); *A61B 50/20* (2016.02); *A61B 50/30* (2016.02); *A61B 50/33* (2016.02);
(Continued)

(58) Field of Classification Search
CPC ......... A61B 50/20; A61B 50/22; A61B 50/30; A61B 50/33; A61B 50/34;
(Continued)

(56) References Cited

U.S. PATENT DOCUMENTS 3,890,096 A 6/1975 Nichol et al.
4,135,868 A 1/1979 Schainholz
(Continued)

FOREIGN PATENT DOCUMENTS

DE 29714090 U1 10/1997
WO WO-98/47542 A1 10/1998
(Continued)

OTHER PUBLICATIONS

Supplementary European Search Report, European Patent Application No. EP13808831, dated Jan. 13, 2016.
(Continued)

*Primary Examiner* — Timothy Cleveland
(74) *Attorney, Agent, or Firm* — Marshall, Gerstein & Borun LLP

(57) ABSTRACT

Sterilization cassette systems, instrument retention systems for use with a sterilization cassette, and configurable instrument retention members are disclosed that are suitable at least for holding medical and/or dental instruments during sterilization in an autoclave.

8 Claims, 10 Drawing Sheets

(51) Int. Cl.
  *A61B 50/20* (2016.01)
  *A61B 50/30* (2016.01)
  *A61B 50/33* (2016.01)
  *A61B 50/00* (2016.01)
(52) U.S. Cl.
  CPC ...... *A61B 50/34* (2016.02); *A61B 2050/0056* (2016.02); *A61L 2202/182* (2013.01); *A61L 2202/24* (2013.01)
(58) Field of Classification Search
  CPC .............. A61B 2050/0056; A61L 2/26; A61L 2202/182; A61L 2202/24
  See application file for complete search history.

(56) References Cited

U.S. PATENT DOCUMENTS

| | | | |
|---|---|---|---|
| 4,854,475 A * | 8/1989 | Riihimaki | A61L 2/26 206/369 |
| 5,215,726 A | 6/1993 | Kudla et al. | |
| 5,433,929 A | 7/1995 | Riihimaki et al. | |
| 5,451,379 A | 9/1995 | Bowlin, Jr. | |
| 5,492,671 A | 2/1996 | Krafft | |
| 5,540,901 A | 7/1996 | Riley | |
| 5,759,502 A | 6/1998 | Spencer et al. | |
| 6,193,932 B1 | 2/2001 | Wu et al. | |
| 7,544,336 B2 | 6/2009 | Powell | |
| 2007/0212277 A1 | 9/2007 | Riley | |
| 2013/0334083 A1 | 12/2013 | Bugnard et al. | |
| 2014/0348722 A1 | 11/2014 | Gray-Dreizler et al. | |

FOREIGN PATENT DOCUMENTS

| | | |
|---|---|---|
| WO | WO-98/50083 A1 | 11/1998 |
| WO | WO-2012/084198 A1 | 6/2012 |
| WO | WO-2012/084199 A1 | 6/2012 |

OTHER PUBLICATIONS

International Search Report and Written Opinion for Application No. PCT/US2013/047606, dated Jan. 31, 2014.

* cited by examiner

STERILIZATION CASSETTE SYSTEMS, INSTRUMENT RETENTION SYSTEMS FOR A USE WITH A STERILIZATION CASSETTE, AND CONFIGURABLE INSTRUMENT RETENTION MEMBERS FOR USE THEREWITH

BACKGROUND

1. Field of the Application

The present patent application relates generally to apparatus for sterilizing and storing medical/dental instruments, such as sterilization cassettes and/or portions of sterilization cassettes and/or sterilization cassette systems and/or instrument retention members and systems for use with sterilization cassettes, either individually or in various combinations thereof.

2. Background

Medical and dental instruments generally need to be sterilized prior to use on a patient. Instruments that are to be used multiple times on different patients or procedures need to be sterilized prior to each use. Therefore, medical or dental professionals typically sterilize these instruments near the operating or treatment area, such as in the office or hospital.

Instruments are often sterilized using an autoclave. An autoclave generally has a compartment into which the unsterile instruments are placed. The compartment is closed, and steam and/or hot water is injected into the compartment for a period of time sufficient to sterilize the instruments. Thereafter, the compartment is opened and the sterilized instruments are removed and, optionally, stored for later use.

Sterilization cassettes are containers used to hold instruments during sterilization and, optionally, to store the sterilized instruments at least temporarily after sterilization. Sterilization cassettes typically have a body defining one or more trays for holding the instruments. The trays typically have a closed position, in which the instruments are held within an enclosed, porous compartment surrounded by and/or between the trays, and an open position, in which the instruments may be removed from the trays.

In a typical sterilization cassette 10 shown in FIG. 1, the body is defined by two opposing cassette trays 12, 14 connected in a clamshell configuration. Instrument retention members 16, 18 are carried by one or both trays 12, 14 for releasably retaining one or more instruments (not shown). The two trays 12, 14 are secured together in a closed position, in which the instruments are located inside a compartment 20 defined between the two trays and held in a fixed position by and between the instrument retention members 16 and 18. Each tray has a porous wall 22, 24 that allows the hot water and/or steam to enter into the compartment 20 to sterilize the instruments therein while in an autoclave.

The present applicants have identified a need for improvements to the typical sterilization cassette.

SUMMARY

Various aspects of the present application include sterilization cassette systems, instrument retention systems for use with a sterilization cassette, and configurable instrument retention members as shown, described, and/or claimed herein.

The systems and members disclosed herein are preferably suitable for holding medical and/or dental instruments, for example, during sterilization in an autoclave.

Other aspects and advantages of the present disclosure will become apparent upon consideration of the following detailed description.

DETAILED DESCRIPTION

Figure 1:
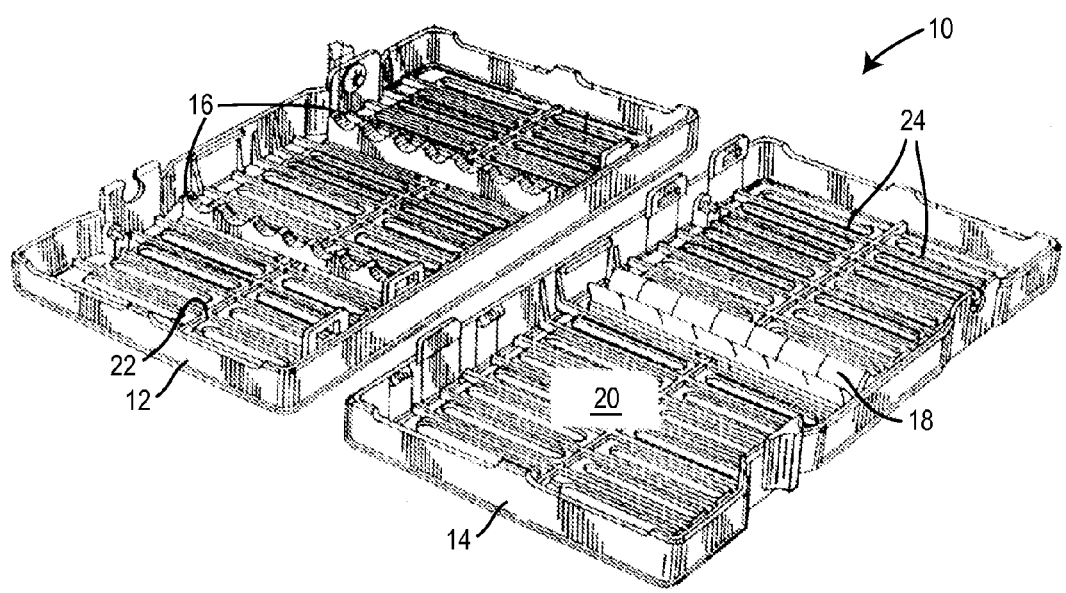
FIG. 1 is an isometric view of a prior art sterilization cassette.
Figure 2:
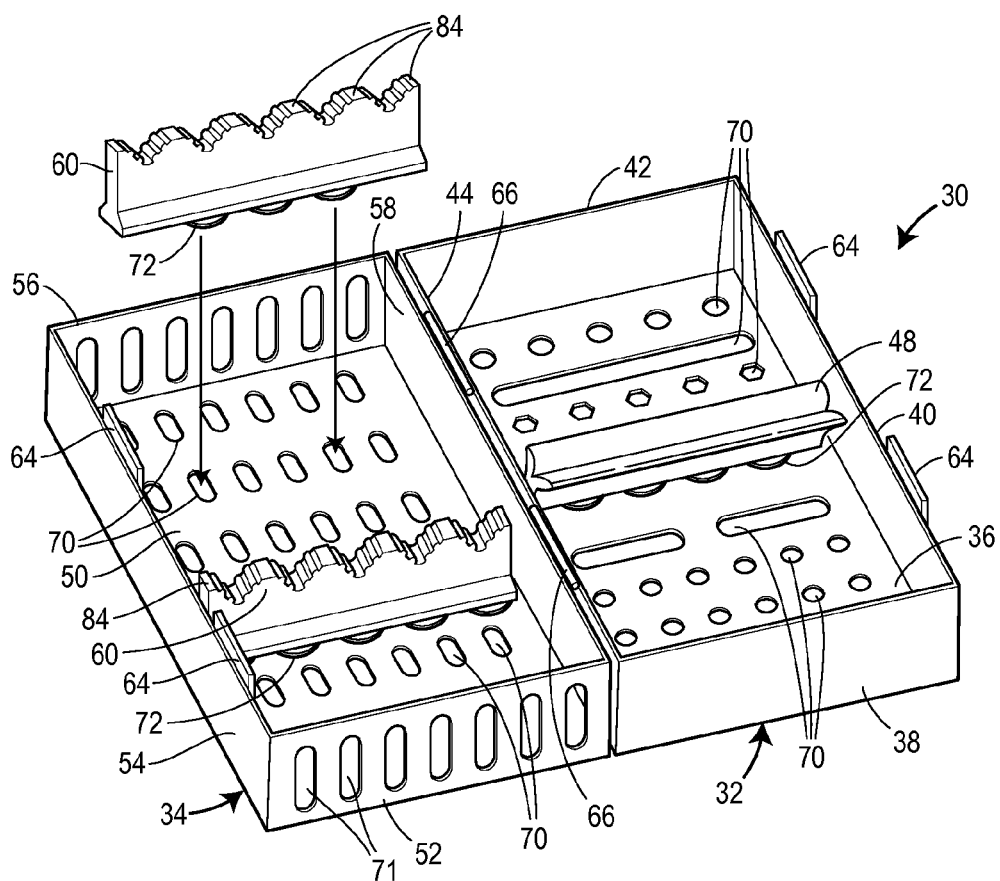
FIG. 2 is an isometric view of a sterilization cassette system with configurable instrument retention members according to one aspect of the present application.
Figure 2A:
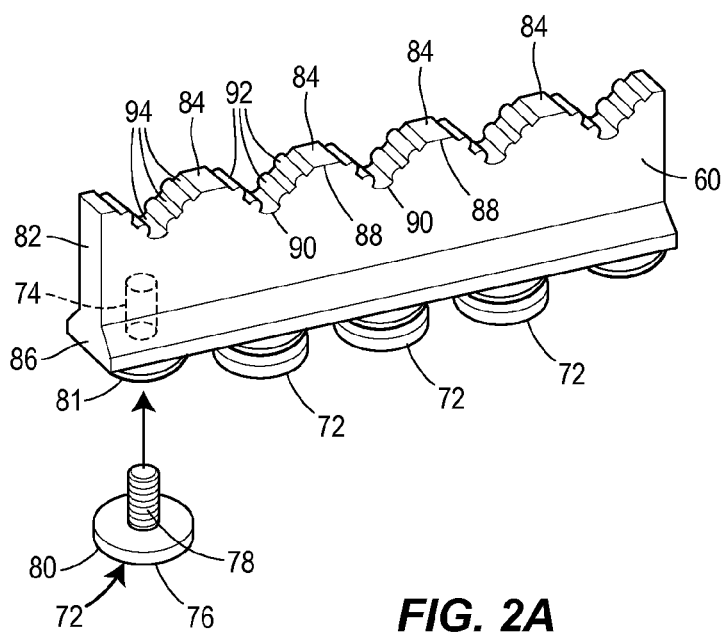
FIG. 2A is an enlarged isometric detail view of an instrument retention rail of FIG. 2.

Turning now to the drawings, FIGS. 2 and 2A show a first exemplary sterilization cassette system including a sterilization cassette 30 for holding medical and/or dental instruments (not shown) during a sterilization procedure, for example in an autoclave, and an instrument retention system with configurable instrument retention members adapted to be used with the sterilization cassette 30. The sterilization cassette 30 has a body defined by opposing top and bottom cassette trays 32, 34. (All relational directional terms used herein, such as top, bottom, left, right, and the like, are used solely for convenience of description with respect to the drawings and are not otherwise intended as limiting the structural feature so modified.) The cassette trays 32, 34 have an open position as shown in FIG. 2 and a closed position. In the closed position, the top tray 32 is connected to the bottom tray 34 in a clamshell arrangement to form an interior compartment therebetween. The interior compartment is sized and shaped to receive one or more instruments, such as medical instruments and/or dental instruments, completely therein when the trays are in the closed position. In the open position, the interior surfaces of the trays 32, 34 are exposed as seen in FIG. 2, and instruments may be inserted or removed from the trays 32, 34. The sterilization cassette 30 is adapted to be used with different instrument retention systems, including various configurable instrument retention members that can be easily selectively arranged in many different arrangements and configurations as desired by a user, as disclosed in various examples hereinafter.

Each of the trays 32, 34 has a generally rectangular configuration; however, the trays are not limited to the rectangular configuration of this exemplary embodiment. The top tray 32 has a rectangular main wall 36 and four peripheral sidewalls 38, 40, 42, 44 depending upwardly from and surrounding the outer periphery of the main wall 36. The bottom tray 34 likewise has a rectangular main wall 50 and four peripheral sidewalls 52, 54, 56, 58 depending upwardly from and surrounding the outer periphery of the main wall 50. In this exemplary arrangement, the sterilization cassette 30 is shown with configurable instrument retention members that include a compression rail 48 and a pair of first and second instrument locating rails 60. The compression rail 48 is releasably connected to the main wall 36, and the instrument locating rail 60 is releasably connected to the main wall 50. Releasable connectors, such as clips 64 and/or hinges 66 are carried by opposing sidewalls 40, 44, 50, 58 and arranged to releasably secure the top and bottom trays 32, 34 together with the distal edges of the sidewalls 38, 40, 42, 44 engaged against the distal edges of the sidewalls 52, 54, and 58 to define the interior compartment therebetween in the closed position. Each tray 32, 34 has one or more porous walls as described hereinafter arranged to allow steam and/or hot water to enter into the interior compartment when the trays 32, 34 are in the closed position.

Each of the main walls 50 and 36 includes a plurality of openings 70, and each of the instrument locating rail 60 and the compression rail 48 includes a plurality of connectors 72 adapted to secure the rail to the main walls 50 or 36 through the openings 70. The openings 70 are arranged in an array adapted to allow the rails 48, 60 to be connected to the main walls 50 and/or 36 in a plurality of different positions and arrangements. In a preferred arrangement, the openings 70 are arranged in an array that forms multiple rows of openings, wherein each row is arranged so as to align each connector 72 of one of the rails with a corresponding hole 70. The openings 70 may have any shape capable of receiving the connectors 72, such as circular, oval, or polygonal. Further, the openings 70 may form elongate slots that extend partially or completely across the respective main wall 50 and/or 36, such that one opening 70 may receive more than one connector 72. In any arrangement, the openings 70 preferably provide through-passages for water and/or steam to enter into the interior compartment when the trays 32, 34 are in the closed position. The openings 70 may also be formed in any number of different arrangements or shapes so as to provide an aesthetically pleasing appearance to the cassette 30.

Optionally, additional holes 71 may be located in any or all of the sidewalls 38, 40, 42, 44, 52, 54, 56, 58 and/or main walls 50 and/or 36 to provide additional through-passages for water and/or steam to enter into the interior compartment when the trays 32, 34 are in the closed position. The holes 71 may be formed in any number of different shapes and/or arrangements so as to provide an aesthetically pleasing appearance to the cassette 30.

The connectors 72 are adapted to interact with the openings 70 to releasably connect the rails 48, 60 to the respective main wall 50 and/or 36. In one arrangement, each connector 72 has the form of a plug member sized to lockingly fit into any one of the openings 70. The plug member includes an enlarged resilient head or resilient prongs arranged to snap-fit into the opening 70. In another arrangement, each connector 72 includes a threaded bore 74 extending upwardly into a bottom surface of the respective rail and a cap screw 76 having a threaded shaft 78 arranged to be threadedly received in the threaded bore 74 and an enlarged head 80, such as a flange or washer. Optionally, a clamp surface 81, such as a washer or flange, is disposed on the bottom surface of the rail surrounding the threaded bore 74. The threaded bore 74 aligns with an opening 70 on an interior side of the floor 50 or ceiling 36, and the threaded shaft 78 is received through the opening 70 and into the threaded bore 74 with the enlarged head 80 disposed on an exterior side of the main wall 50 or 36, thereby clamping the respective main wall between the enlarged head 80 and the rail or the clamping surface 81. Other forms of the connectors 72 sufficient to interact with the openings 70 to releasably secure the rails 48, 60 to the main wall 50 and/or 36 may also be used.

As best seen in FIG. 2A, each instrument locating rail 60 has an elongate vertical rib 82 extending from a left end to a right end, a plurality of scallops 84 formed along a top edge of the vertical rib 82, a base portion 86 extending along a bottom edge of the vertical rib 82, and a plurality of connectors 72 along the bottom of the base portion 86. Each scallop 84 is in the form of an arched surface, such as an arcuate or polygonal shape. The scallops 84 define a series of alternating peaks 88 and valleys 90 along the top edge of the rib 82. In use, an instrument, such as a medical or dental instrument, rests in a valley 90 between adjacent scallops 84.

Each scallop 84 further includes one or more nubs, such as ridges 92, along the top surface thereof to minimize the contact area between the top surface of the instrument locating rail 60 and an instrument carried in any one of the valleys 90. The nubs preferably also form channels 94 extending from a front side of the vertical rib 82 to a back side of the vertical rib sufficient to allow steam and/or water to pass between the front and back sides. The ridges 92 are aligned transverse to the longitudinal axis of the vertical rib 82. The ridges 92 are spaced apart thereby forming the channels 94 to allow water and/or steam to pass between the scallops 84 and an instrument carried in a valley 90. Each scallop 84 includes two ridges 92 on either side of the peak 88. However, other shapes, arrangements, numbers, and/or sizes of nubs may also be used as long as the nubs minimize contact area between the instrument locating rail 60, 62 and the instrument. For example, the nubs may be in the form of mounds, fingers, or a knobby top surface of the scallops 84. The instrument locating rail 60 may be made of resilient material, such as silicone rubber, or non-resilient material, such as metal or hard thermoplastic, or combinations thereof.

The compression rail 48 may take various forms suitable for holding instruments in place against the instrument locating rails 60. In one arrangement, the compression rail 48 is formed of a resilient material, such as silicone rubber, and presses the instruments against the instrument locating rails 60. The compression rail 48 has an elongate vertical rib with a plurality of connectors 72 disposed along a bottom edge of the vertical rib. A top edge of the vertical rib is split along a longitudinal axis of the vertical rib forming a pair of laterally curving left and right flaps that engage any instruments carried by the instrument locating rails 60.

As shown in the exemplary arrangement of FIG. 2, two instrument locating rails 60 are carried on the interior surface of the main wall 50, and one compression rail 48 is carried on the interior surface of the main wall 36. The compression rail 48 is arranged to be parallel with and disposed between the two instrument locating rails 60 when the top and bottom trays 32, 34 are arranged in the closed position. In this manner, the compression rail 48 is arranged to hold any instruments carried on the instrument locating rails 60 in place when the trays 32, 34 are in the closed position. Preferably, the scallops 84 of the instrument locating rails 60 are aligned such that the valleys 90 are aligned to allow an instrument to be located parallel to the sidewalls 54, 58 when located therein. However, more or fewer instrument locating rails 60 and compression rails 48 may be secured to the main walls 50 and/or 36 and/or placed in different arrangements.

Figure 3:
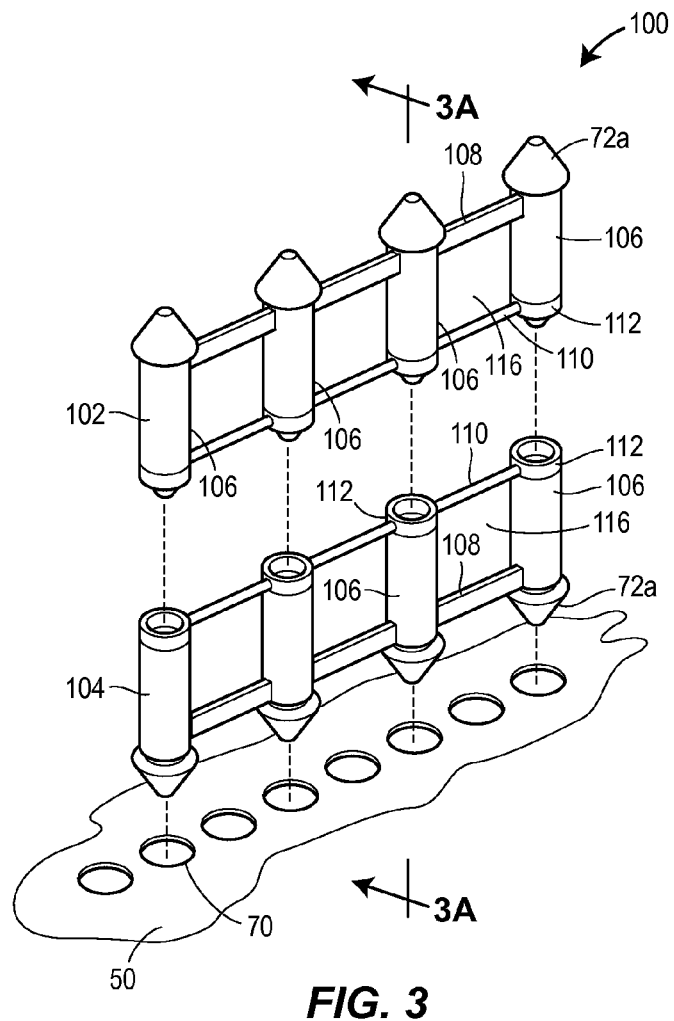
FIG. 3 is a partial isometric view of a pair of configurable instrument retention members according to another aspect of the present application in a spaced apart open position and a tray.
Figure 3A:
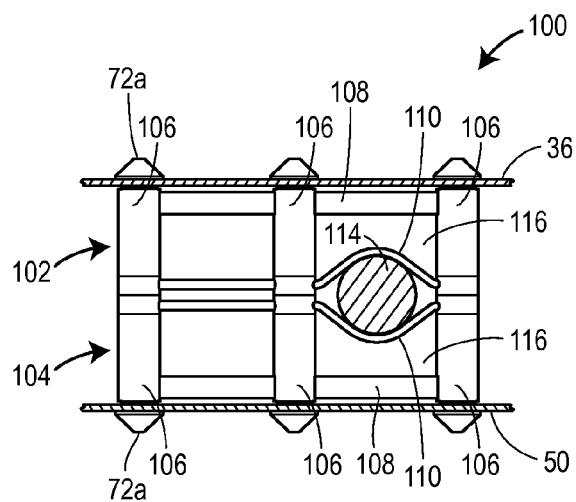
FIG. 3A is an elevational cross-sectional view of the configurable instrument retention members and the tray along the lines 3A-3A of FIG. 3 in a closed position and with an instrument clamped therebetween.

FIGS. 3 and 3A show another instrument retention system 100 with configurable instrument retention members for use in a sterilization and storage system, such as with the sterilization cassette 30. The configurable instrument retention members include an upper compression rail 102 and a lower retention rail 104. The upper compression rail 102 is arranged to depend downwardly into the interior compartment from the main wall 36. The upper compression rail 102 releasably connects to the main wall 36 by a plurality of connectors 72a arranged to be secured through the openings 70. Similarly, the lower compression rail 104 is arranged to project upwardly into the interior compartment from the main wall 50 and releasably connects to the main wall 50 by a plurality of connectors 72a arranged to be retained through the openings 70. Preferably, the upper and lower compression members 102, 104 are secured to the interior sides of the main walls 36 and 50, respectively, of the sterilization cassette 30 so as to be aligned in immediate opposition to each other when the trays 32, 34 are in the closed position as shown in FIG. 3A.

The compression rails 102, 104 are largely similar to each other except as otherwise described herein. Each compression rail 102, 104 includes a plurality of vertical posts 106 that are spaced apart laterally and connected by a compression member 110 in an arrangement that resembles a picket fence. The posts 106 of each compression rail 102, 104 preferably are also connected by a rigid cross member 108. Each post 106 extends between opposite first and second ends. A connector 72a is disposed at the first end, and an alignment member 112 is disposed at the second end.

The connector 72a is in the form of a head, for example a narrow neck portion connected to the first end of the post 106 and a conical or frustoconical head disposed at a distal end of the neck portion, that snap-fits into an opening 70. The neck portion has a smaller diameter than the second end of the post 106 and the larger diameter of the frustoconical head is adjacent the neck portion. In one arrangement, the head may be made of resilient material, such as silicone rubber, to allow insertion into and extraction out of the opening 70. In another arrangement, the head may be formed of a rigid material, such as metal or rigid thermoplastic. The head may be fixedly attached to the post 106 or the head may be removably secured to the post. For example, the head may screw onto the post 106, such as by a threaded joint between the neck and the head and/or a threaded joint between the neck and the post. The connectors 72a may take other forms capable of releasably interlocking with the openings 70, such as described elsewhere herein.

A rigid cross member 108 optionally extends between each adjacent pair of posts 106 and is attached to each of the posts adjacent the connector 72a at the second end of the post. The rigid cross members 108 are sized to locate the posts 106 at a distance apart equal to a regular predefined distance between openings 70 in either the main wall 36 and/or 50, such as at every other opening 70 in a row of the openings. Preferably, the rigid cross members 108 on each compression rail 102, 104 are aligned along a common longitudinal axis.

The alignment members 112 are arranged to align and optionally to slip fit the second ends of the posts 106 of the upper compression rail 102 with the second ends of the posts 106 of the lower compression rail 104. The alignments members 112 may have substantially identical shapes that will slip fit with each other when engaged in opposing relation. Alternatively, the alignment members 112 on the upper rail 102 may have a different shape than the alignment members 112 on the lower compression rail 104. For example, the alignment members 112 carried by the lower rail 104 may have a female portion, such as a central bore or socket, and the alignment members 112 carried by the upper rail 102 may have a male portion, such as shaft or knob, that is received within the female portion. The alignment members 112 may be permanently secured to the posts 106 or the alignment members 112 may be removably secured to the posts 106, for example, to allow different configurations of the posts 106 and the alignment members 112 to be formed.

A compression member 110 extends between each adjacent pair of posts 106 and is attached to each of the posts adjacent alignment member 112 at the first end of the post. The compression members 110 may be integral with the alignment members 112 or separate from the alignment members 112. The compression member 110 optionally is made of a band of soft durometer resilient material, such as silicone rubber, that is sufficient to resiliently engage and accommodate an instrument.

As best seen in FIG. 3A, the compression members 110 are arranged such that an instrument 114 is captured between opposing compression members 110 of the upper and lower compression rails 102, 104 when the alignment members 112 of the upper compression rail 102 are slip fit with the alignment members 112 of the lower compression rail 104. Preferably, the opposing compression members 110 are arranged to stretch and/or resiliently deform around the instrument 114 to securely capture the instrument therebetween.

An opening or window 116 may be defined between each adjacent pair of posts 106 and the rigid cross member 108 and the compression rail 110 on each compression rail 102, 104. In one arrangement, the compression member 110 is spaced vertically along the posts 106 away from the rigid cross member 108, thereby defining the windows 116 therebetween. In some instances, irregularly shaped instruments or portions thereof might not be amendable to being securely captured between the opposing compression members 110 of the upper and lower compression rails 102, 104 as shown in FIG. 3A. In such instances, it may be possible to insert the instrument through one or more of the windows 116 to hold the instrument in a selected position, for example, in the interior compartment of the sterilization cassette 30.

Figure 4:
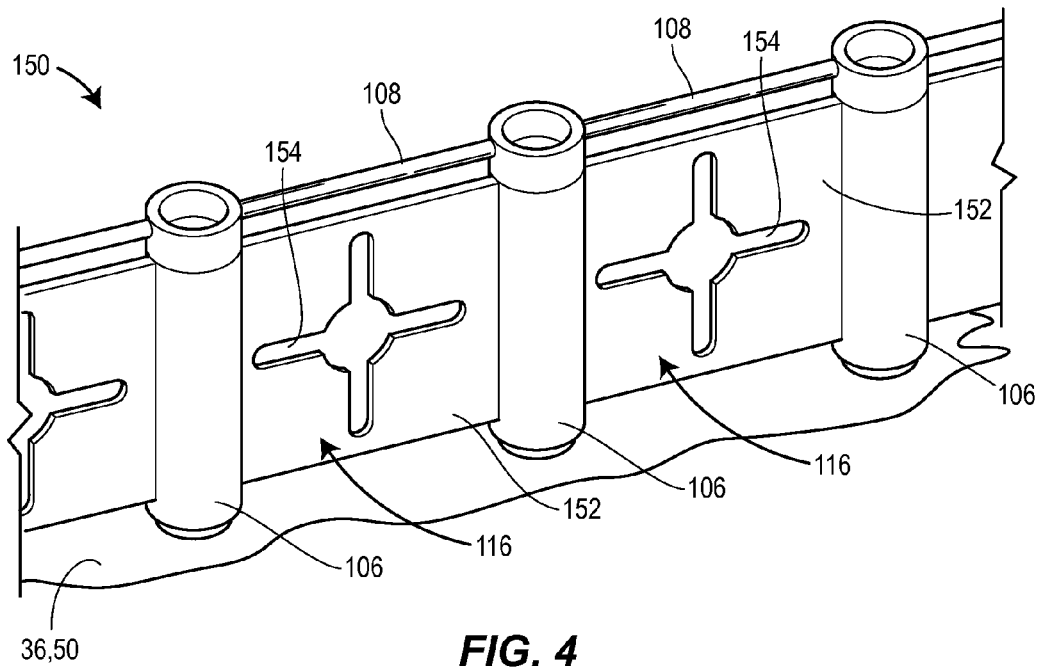
FIG. 4 is an enlarged isometric partial view of another configurable instrument retention member according to a further aspect of the present application.
Figure 4A:
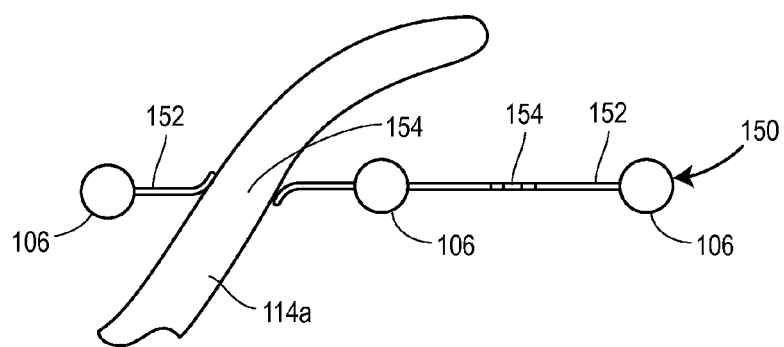
FIG. 4A is a top plan view of the configurable instrument retention member of FIG. 4 and with a handle of a hinged instrument received therein.

FIGS. 4 and 4A show another instrument retention system with a configurable instrument retention member in the form of an instrument locating rail 150. The instrument locating rail 150 is similar in design to the compression rails 102, 104 in that the locating rail 150 includes a plurality of posts 106 spaced apart and arranged with connectors 72 or 72a (not shown) at one end to releasably secure the posts through the openings 70 of the main walls 36 and/or 50 of the trays 32, 34 as described previously herein. However, unlike the compression rails 102, 104, a web 152 at least partially covers each of one or more of the windows 116 between the posts 106. Further, the compression members 110 and alignment members 112 may optionally be omitted, and the rigid cross members 108 may be aligned adjacent either end of the posts 106. In one optional arrangement, the compression members 110 and the rigid cross members 108 are omitted, and the posts 106 are connected by the webs 152 alone. The web 152 is preferably made of a resilient, deformable material, such as silicone rubber.

Slits 154 are disposed through the web 118 to receive a portion of an instrument, such as an irregularly shaped handle 114a of a hinged instrument, such as pliers or a clamp. The slits 154 may take any shape sufficient to allow the web 152 to engage and thereby to securely hold the instrument, for example, during sterilization in an autoclave. In the depicted arrangement, the slits 154 form the shape of a cross having an elongate horizontal slot crossing with an elongate vertical slot and a circular cutout where the horizontal and vertical slots would intersect. Other varied shapes and sizes of the slits 154 sufficient to receive and hold a portion of an instrument may also or alternatively be used.

Figure 5:
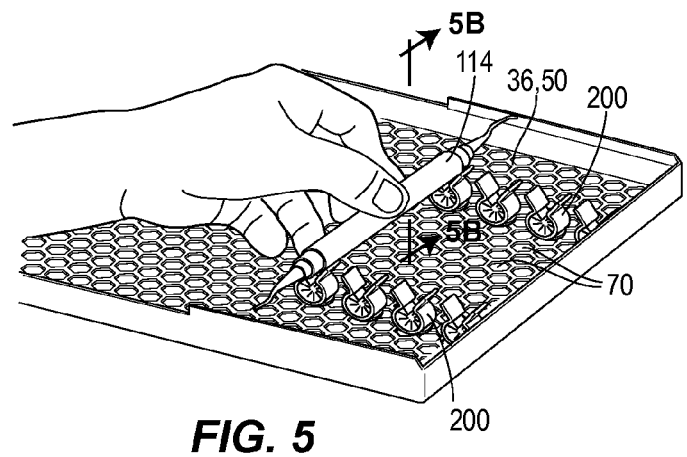
FIG. 5 is an isometric view of another instrument retention system according to yet another aspect the present application.
Figure 5A:
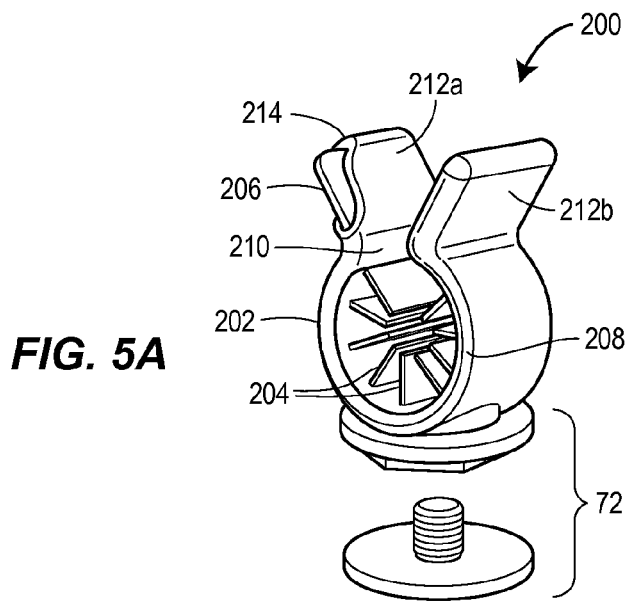
FIG. 5A is an enlarged isometric view in partial cutaway of a configurable retention member shown in FIG. 5.
Figure 5B:
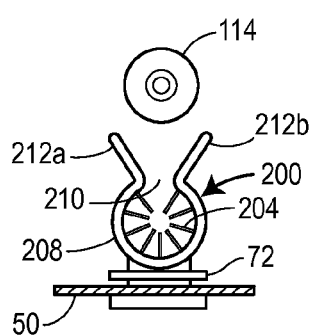
FIGS. 5B-5D are enlarged elevational cross-sectional views of the instrument retention system along the lines 5B-5B of FIG. 5.
Figure 5C:
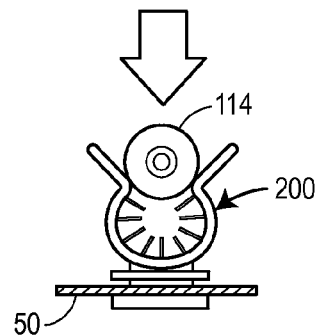
Figure 5D:
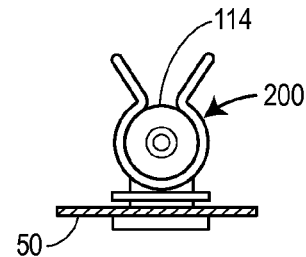

In FIGS. 5-5D, another instrument retention system with configurable instrument retention members includes one or more instrument clips 200 that can be secured to the trays 32, 34 through the openings 70 of the main walls 36 and/or 50. The instrument clips 200 are sized to fit inside of the interior compartment of the sterilization cassette 30 when the trays 32, 34 are in the closed position and to releasably clip around a portion of the instrument 114, such as a cylindrical handle portion. Each instrument clip 200 includes a clip spring 202, a connector 72, and one or more flexible fingers 204. The clip spring 202 is a resilient member arranged to releasably clamp onto an instrument in a manner sufficient to hold the instrument in a selected position inside the interior cavity of the sterilization cassette 30. The connector 72 is arranged to allow the instrument clip 200 to be secured to the trays 32, 34 in any of a plurality of selected positions. The flexible fingers 204 are arranged to minimize point contact with and/or to provide positive gripping of an instrument held by the clip spring 202. The flexible fingers 204 preferably also provides for flow of water and/or steam through the instrument clip 200 around the instrument 114 and through the sterilization cassette 30 in general.

The clip spring 202 in one arrangement is formed of a strip 206 of resilient material, such as stainless spring steel, shaped to form an expandable clamp 208, a narrow throat 210 that opens into the clamp 208, and a pair of guide members 212a, 212b that flare outwardly from the throat 210. The clamp 208 is defined by a central portion of the strip 206 shaped as a partial tube that defines a through bore, such as a C-section tube that defines a circular bore, adapted to clamp the instrument 114 therein. The throat 210 is defined by a gap between opposite ends of the partial tube of the clamp 208. The gap of the throat 210 is sized to allow the instrument 114 to be inserted through the throat 210 into the bore of the clamp 208. The throat 210 preferably has a width that is less than a largest corresponding width across the bore of the clamp 208. Each guide member 212a, 212b is an opposite distal end portion of the strip 206 that projects from the corresponding end of the partial tube away from the clamp 208. Preferably, the guide members 212a, 212b taper to form a funnel-shaped guide-way that tapers together from the distal ends of the strip 206 to the throat 208. The clip spring 202 may be formed from a single piece of material, as described above, for example by bending or may be formed of multiple separate pieces of material that are joined together in any suitable manner, such as by soldering or fasteners.

The connector 72 is substantially the same as the connector 72 shown in FIG. 2A, although other forms of connectors sufficient to releasably lock the instrument clip 200 through one of the openings 70, such as the connectors 72a, may be used.

The flexible fingers 204 project radially inwardly from an inner periphery of the clamp 208 into the bore. The flexible fingers 204 may be formed as part of an outer sheath 214, for example an overmold made of silicone rubber, enveloping the entire strip 206 of resilient material and optionally a portion of the connector 72 that is permanently attached to the clip spring 202. In FIG. 5A, the outer sheath is shown partly cut away for ease of reference. The flexible fingers 204 extend toward a central region of the bore, such as an axis of the circular bore. The flexible fingers 204 are spaced apart circumferentially around the inner periphery of the clamp 208. Each flexible finger 204 optionally has the form of a flat flap. The flexible fingers 204 form channels that are arranged to allow steam and/or water to pass longitudinally through the bore, for example with each flap arranged parallel with a longitudinal axis of the circular bore, preferably extending through the longitudinal axis. Nine flexible fingers 204 are shown in the figures; however, the instrument clip 200 may include more or fewer flexible fingers 204. The distal ends of the flexible fingers 204 are spaced from the longitudinal axis of the partial circular bore, thereby providing an open central area along the longitudinal axis.

As shown in FIG. 5, the instrument clips 200 are preferably arranged in pairs in one of the trays 32, 34 of the sterilization cassette 30. The handle of the instrument 114 is releasably clipped into a corresponding pair of the instrument clips 200. FIGS. 5B, 5C, and 5D show the instrument 114 being inserted into the instrument clip 200 connected to the main wall 50 of the lower tray 34. In FIG. 5B, the handle of the instrument 114 is disposed over the instrument clip 200 above the throat 210. In FIG. 5C, the handle of the instrument 114 is in the guide-way between the guide members 212a, 212b and part way into the throat 210. In FIG. 5D, the handle of the instrument 114 is completely nested into the bore of the clamp 208. The handle of the instrument 114 is larger than the bore, and the clamp 208 resiliently clamps against the handle. The flexible fingers 204 are flexed around the handle against the inner periphery of the clamp 208. If the handle of the instrument 114 were to be smaller than the bore, then the flexible fingers 204 would grip against the handle to secure the instrument in the bore. To remove the instrument, the instrument is pulled back out of the clamp 208 through the throat 210.

Figure 6:
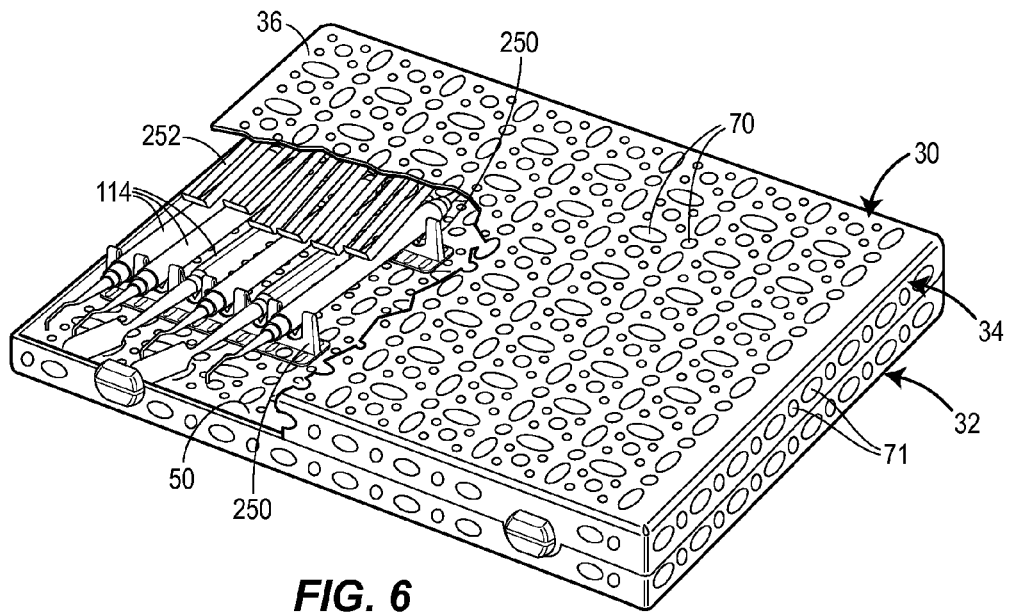
FIG. 6 is an isometric view in partial cutaway of a sterilization cassette system including an instrument retention system according to a further aspect of the application.
Figure 6A:
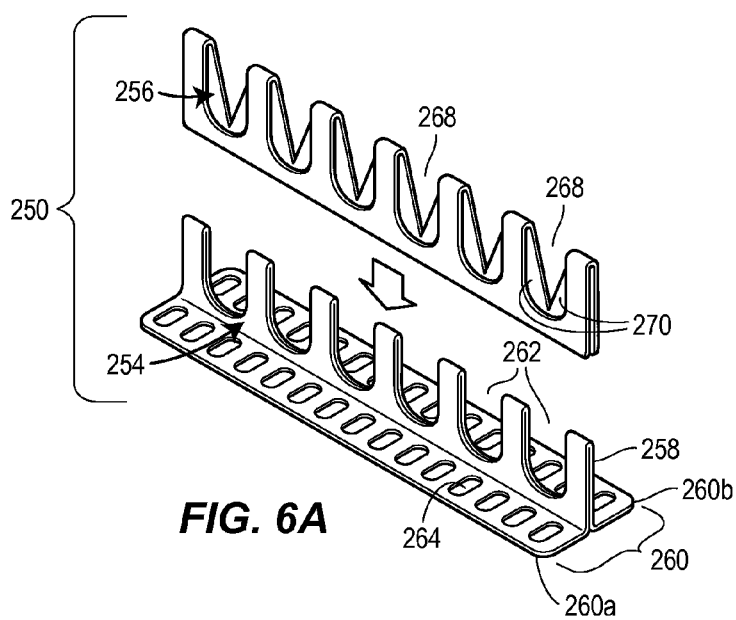
FIGS. 6A and 6B are enlarged isometric view of configurable instrument retention members shown in FIG. 6.
Figure 6B:
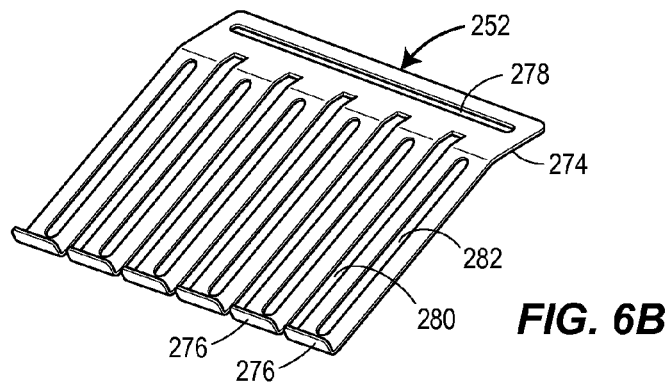

FIGS. 6, 6A, and 6B show another instrument retention system with configurable instrument retention members adapted to be used with the sterilization cassette 30. The configurable instrument retention members include a pair of instrument locating rails 250 for receiving one or more instruments 114 therein and a compression spring rail 252 for holding the instruments in the instrument locating rails 250.

Each instrument locating rail 250 preferably includes a support skeleton 254 made of a rigid material, such as stainless steel or a hard thermoplastic, and a cover 256 made of a soft resilient material, such as silicone rubber. The cover 256 is carried by the support skeleton 254. The cover 256 is releasably attached to the skeleton so as to be replaceable. However, the instrument locating rail may be formed of fewer or more, individual components sufficient to function to hold instruments as described herein.

The support skeleton 254 includes an elongate vertical rib 258 extending between two opposite ends, a connector base 260 disposed along a bottom edge of the vertical rib 258, and one or more recesses 262 along a top edge of the vertical rib 258. The connector base 260 includes opposite left and right lateral flanges 260a, 260b extending laterally left and right, respectively, from the bottom edge of the vertical rib 258, and one or more connector holes 264 through one or both of the left and right lateral flanges 260a, 260b. The connector base 260 may extend the complete length between the opposite ends of the vertical rib 258 or may extend partially or intermittently therealong. Preferably, a plurality of the recesses 262 extend substantially the entire length of the vertical rib 258 as shown in the drawings. Each recess 262 is arranged to accommodate receiving a portion of an instrument 114, such as the instrument handle. For example, each recess 262 may have a U-shape as shown in FIG. 6A; however, other suitable shapes are also contemplated. The recess 262 is preferably oversized, i.e., larger than the anticipated instrument 114, to accommodate the added thickness of the cover 256.

The cover 256 is also in the shape of an elongate vertical rail shaped and sized to cover the vertical rib 258 with a series of slots 268 along a top edge. The cover 256 has a left side and right side and one or more pockets (not visible) extending upwardly from a bottom edge between the left and right sides for receiving the support skeleton 254 therein. The slots 268 along the vertical rail are arranged to correspond with the recesses 262 along the support skeleton 254. When the cover 256 is operatively disposed on the support skeleton 254, the slots 268 in the cover 256 are located in corresponding recesses 262 of the support skeleton 254. Each slot 268 is sized to receive a portion of an instrument 114, such as the instrument handle.

The cover 256 also includes at least one, and preferably two, thin webs 270, or fins, in each slot 268. Each web 270 forms a tapered resilient elastic surface arranged to grip the instrument 114 and/or form a resilient elastic surface to receive instruments of different sizes and/or provide a soft surface that may provide a gentle receiving surface for delicate instruments. The webs 270 are preferably molded as a single piece with the vertical rail. The webs 270 are oriented vertically in the plane of the vertical rail. Each web 270 has a first edge connected to the vertical rail along an inner peripheral edge of the respective slot 268, and a second edge opposite the first edge that spans across a portion of the slot 268. For example, each slot 268 may include two opposing webs 270 along opposite inner peripheral edges sides of the slot 268 in a V-shaped formation that is tapered from a widest space near the mouth of the slot 268 to a narrowest space at the bottom of the slot 268.

The compression spring rail 252 includes a base rail 274 for attachment to either of the main walls 36, 50 and one or more resilient flexible fingers 276 for pressing the instruments 114 into the slots 268 of the cover 256. The compression spring rail 252 is preferably made of a single piece resilient material, such as pressed stainless steel, sufficient to provide spring action suitable for resiliently pressing the instruments 114 into the slots 268 without harming the instruments.

The base rail 274 in the depicted arrangement has an elongate flat shape with an planar engagement surface for engagement against the main wall 36 and/or 50 and an elongate slot 278 arranged to receive one or more screws or other fasteners therethrough. However, the base rail 274 may take any form sufficient for attachment to the main walls 36 and/or 50 for example by means of screws or other fasteners through the openings 70. The compression spring rail 252 may optionally include connectors, such as 72 or 72a, for releasably attaching the compression spring rail 252 to the main walls 36 and/or 50 as described previously.

The flexible fingers 276 project away from the base rail 274 at an angle, for example of between approximately 2 and 45 degrees, such as between approximately 5 and 30 degrees, or between approximately 10 and 15 degrees, in relation to a planar surface for engagement against the main wall 36 or 50. The flexible fingers 276 optionally are spaced apart by an elongate gap 280 extending from the base rail 274 to a distal end of the adjacent flexible fingers 276. Optionally a slot 282 or other cutout or opening is located along a longitudinal axis of each flexible finger 276. The distal end of each flexible finger 276 may be shaped to minimize scratching or otherwise damaging the surface of the instruments 114, for example with a flared or upturned end.

As best seen in FIG. 6, the pair of instrument locating rails 250 are secured to the interior surface of the main wall 50 in aligned arrangement so that the instruments 114 may be carried in parallel arrangement within corresponding pairs of slots 268. The compression spring rail 252 is secured to the interior surface of the main wall 36 with the base rail 274 flat against the main wall 36 and the flexible fingers extending at an angle away from the main wall 36. The compression spring rail 252 is preferably arranged such that each flexible finger 276 is aligned with a corresponding pair of the slots 268 such that the distal end of the flexible finger is located medially between the pair of slots 268 when the top and bottom trays 32, 34 are secured together in the closed position, as shown in FIG. 6. In this position, the flexible fingers resiliently engage the corresponding instruments 114 to maintain the instruments in the respective slots 268.

The instrument retention systems and the configurable instrument retention members disclosed herein may be used interchangeably with each other in various combinations in the sterilization cassette 30. For example, the various instrument locating rails 60, 150, 250 may be used in a sterilization cassette 30 in any combination together and/or with any of the various compression rails 48, 102, 104, and/or the compression spring rail 252. The instrument clips 200 could be used in a sterilization cassette 30 in conjunction with any of the various compression rails 48, 102, 104, and/or the compression spring rail 252. All combinations and arrangements of any and/or all of the configurable instrument retention members 48, 60, 102, 104 150, 200, 250, 252 in a sterilization cassette 30 are possible and expressly included as part of the present disclosure without listing every possible permutation and arrangement.

Figure 7:
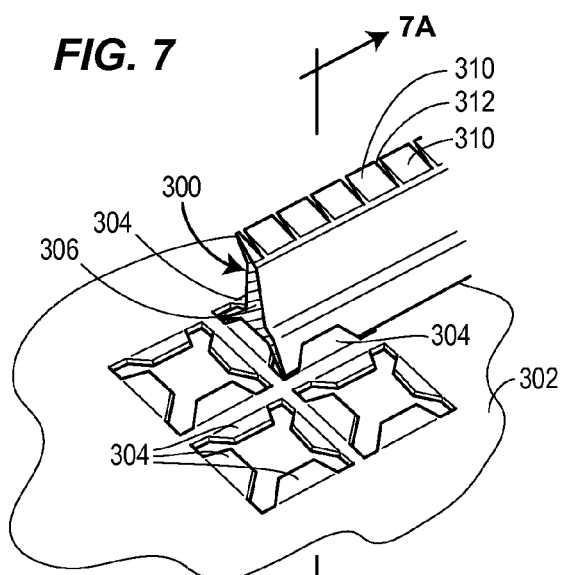
FIG. 7 is a partial isometric view of an instrument retention system according to an additional aspect of the application.
Figure 7A:
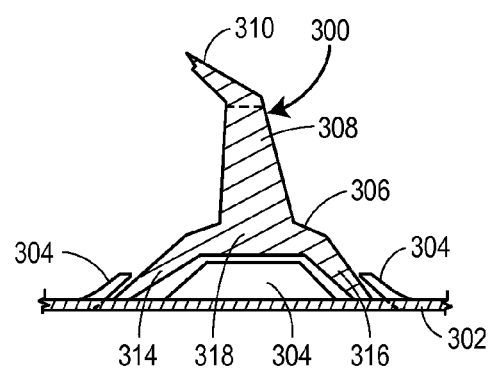
FIG. 7A is a detailed cross-sectional view of the instrument retention system of FIG. 7 along the lines 7A-7A.
Figure 7B:
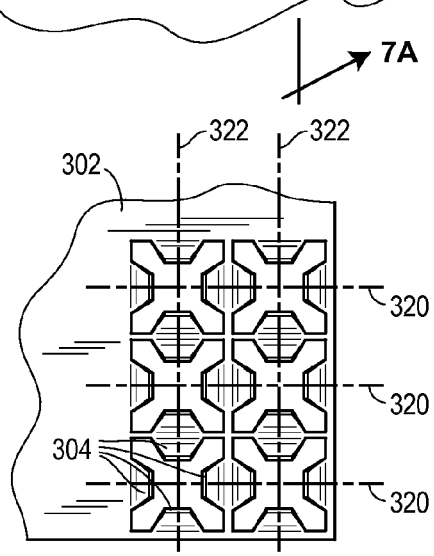
FIG. 7B is a partial plan view of a cassette tray of the instrument retention system of FIG. 7.

FIGS. 7, 7A, and 7B show an instrument retention system with a configurable instrument retention member adapted to be configurably secured to the main wall 302 of a cassette tray, which may be generally similar to the cassette trays 32, 34 except as noted otherwise, with a different connection system than shown previously. The configurable instrument retention member is in the form of an instrument locating rail 300 having an elongate profile extending from a first end of the rail to an opposite second end of the rail. The main wall 302 of the cassette tray includes at least one, and preferably a plurality of opposing pairs of tabs 304 disposed along opposite sides of a row. The tabs 304 are spaced apart on opposite sides of the row, and each pair of opposing tabs 304 in the row is spaced apart along the length of the row. Each tab 304 has a distal end that projects upwardly from the main wall 302 toward the center of the row. The instrument locating rail 300 includes a base 306 that can be selectively engaged with one or more opposing pairs of the tabs 304, such as by fitting into a space between the distal ends of the tabs 304 and the plane of the main wall 302, along a row to secure the instrument locating rail 300 in a selected position on the main wall 302.

As best seen in the cross-sectional profile of FIG. 7A, the instrument locating rail 300 of the exemplary arrangement has an elongate rib 308 projecting upwardly from the base 306 and optionally one or more fins 310 extending upwardly from a top edge of the rib 308. The fins 310 preferably extend at an angle from the rib 308, for example at an angle of between approximately 5 degrees and approximately 85 degrees from a vertical axis of the rib 308. The instrument locating rail 300 may have a single fin 310, for example extending the entire length of the rib 308. Alternatively, the instrument locating rail 300 may have a plurality of fins 310 extending along the length of the rib 308, each adjacent pair of fins 308 being separated by a break, such as a slit 312, cutout, or other separation. The base 306 includes left and right connector flanges 314, 316 projecting from opposite left and right sides of the rib 308, and optionally a horizontal central portion 318 disposed along the bottom edge of the rib 308. The connector flanges 314, 316 project laterally from opposite sides and/or edges of the central portion 318, and optionally are angled downwardly at an angle between approximately 5 degrees and 85 degrees from the horizontal. Preferably, the profile of the base 306 extends continuously between the opposite ends of the instrument locating rail 300, although one or more gaps or breaks may be disposed along the length of the base. The fins 310 may be omitted and/or other structures may be disposed along the top edge of the rib 308 to engage and retain one or more instruments, such as the instruments 114, along the top edge of the instrument locating rail 300. The instrument locating rail 300 is preferably made of a flexible resilient material, such as silicone rubber, and may be made, for example, by extrusion molding or any other process capable of producing the instrument locating rail 300.

As best seen in FIG. 7B, the main wall 302 preferably includes a plurality of tabs 304 arranged to define a plurality of parallel rows 320 and optionally a plurality of parallel columns 322 that intersect the rows 320. The tabs 304 are arranged such that the instrument locating rail 300 may be selectively secured to the main wall 302 along any one of the rows 320 and/or columns 322, for example in a rectangular grid or array as shown in the drawings. For example, a first pair of tabs and a second pair of tabs are aligned along a row, wherein the tabs of each pair of tabs are disposed on opposite sides of the row. A third pair of the tabs and a fourth pair of the tabs form a column that intersects the row, preferably at a right angle. The first pair of tabs of the row 320 are aligned along the column 322 between the third pair of tabs. Although the drawing only shows three rows 320 and two columns 322, this rectangular array can be repeated any number of times. The main wall 302 of the cassette tray is preferably made of a rigid material, such as metal or rigid thermoplastic, and the tabs 304 may be may, for example, by die cutting and pressing or any other process capable of forming the tabs on main wall 302.

To secure the instrument locating rail 300 to the main wall 302, one of the connector flanges 312, 314 is inserted, for example by sliding, underneath one or more tabs 304 on one side of a row 320 or column 322, and the other of the connector flanges 312, 314 is inserted underneath one or more tabs on the opposite side of the row or column, as best shown in FIGS. 7 and 7A. When the tabs 304 are arranged in the rectangular array shown in the drawings, the connector flanges 312, 314 are angled downwardly an amount sufficient form a space underneath the central portion 318 to allow tabs 304 disposed along a central portion of the selected row or column to fit underneath the base 306 without engaging the central portion 318 as best seen in FIG. 7A.

Figure 8:
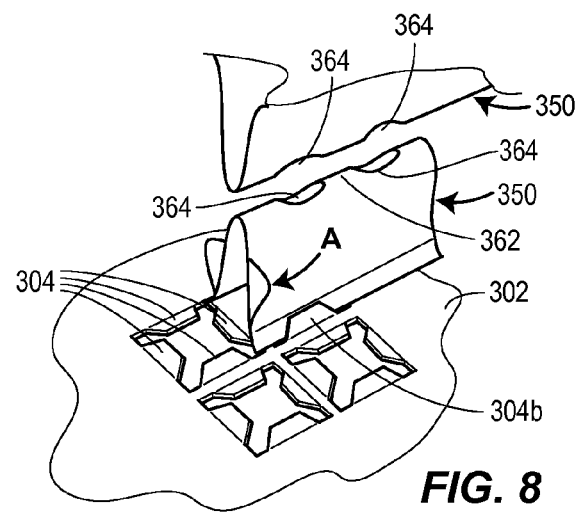
FIG. 8 is a partial isometric view of an instrument retention system according to still another aspect of the application.
Figure 8A:
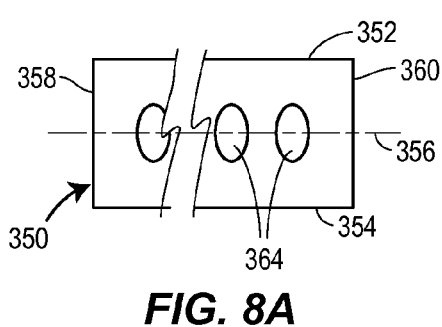
FIGS. 8A and 8B are partial plan and end views of a configurable instrument retention member shown in FIG. 8.
Figure 8B:
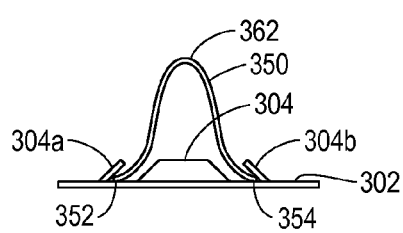

FIGS. 8, 8A, and 8B show another instrument retention system with configurable instrument retention members in the form of instrument locating rails 350 that are also adapted to be selectively configurably secured to the main wall 302 by engaging with opposing pairs of the tabs 304. Each instrument locating rail 350 is in the form of a strip of material, such as metal, thermoplastic, and/or silicone rubber, having a left edge 352 and a right edge 354 extending along opposites sides of a central longitudinal axis 356 between opposite ends 358, 360 of the strip. The strip of material has an arched profile about the longitudinal axis 356 such that the left and right edges 352, 354 depend downwardly from a spine 362 extending along the longitudinal axis 356. The left edge 352 is fitted underneath one or more of the tabs 304a, and the right edge 354 is fitted underneath one or more of the respective opposing tabs 304b. Preferably, the strip of material is resilient a sufficient amount to cause the left and right edges 352, 354 to press laterally outwardly against the opposing pairs of tabs 304a, 304b to releasably secure the instrument locating rail 350 to the main wall 302. Optionally, one or both of the left and right edges 352, 354 is flared outwardly, such as with a curved lateral flare.

The strip of material may be formed to retain the arched profile in an unflexed state. Optionally, strip of material is resiliently flexible such that the strip of material is normally flat in an unflexed state as seen in FIG. 8A and can be readily bent about the longitudinal axis 356 to a flexed stated for securement with the tabs 304a, 304b as seen in FIGS. 8 and 8B. If the strip of material is sufficiently flexible, the spine 362 of the instrument locating rail 300 may flex downwardly, as shown at A, under sufficient pressure, and thereby also function as a resilient compression rail.

One or more receiving recesses 364 are disposed on a top surface of the instrument locating rail 350 along the spine 362. The receiving recesses 364 are arranged to receive a portion of a medical or dental instrument, such as an instrument handle from the instrument 114. The receiving recesses are formed by openings through the strip of material along the longitudinal axis 356; however, the receiving recesses may also be formed by other structures, such as slits and/or pads, for example.

In one possible arrangement, the instrument locating rail 350 is used as part of an instrument retention system in a sterilization cassette as shown in FIG. 8, wherein a first instrument locating rail 350 is secured along a selected row or column of tabs 304 on a first cassette tray, and a second instrument locating rail 350 is secured along a corresponding row or column of tabs 304 on a second cassette tray such that, when the cassette trays are secured together in a closed position generally as described previously herein, the spine 362 of the first instrument locating rail 350 is disposed facing immediately opposite the spine 362 of the second instrument locating rail 350. The instrument locating rails 350 may be sized to leave a gap between the opposing spines 362 in the closed position, or the instrument locating rails 350 may be sized to engage against each other along the spines 362. Further, the instrument locating rails 350 may be sized to compress against each other along the spines 362 if the material is sufficiently flexible to allow the strips of material to flex, such as shown at A.

As with previously described configurable instrument retention members, two or more of the instrument locating rail 350 may be used together or with any one or more of others of the instrument retention members disclosed herein to form an instrument retentions system in a sterilization cassette system.

Figure 9:
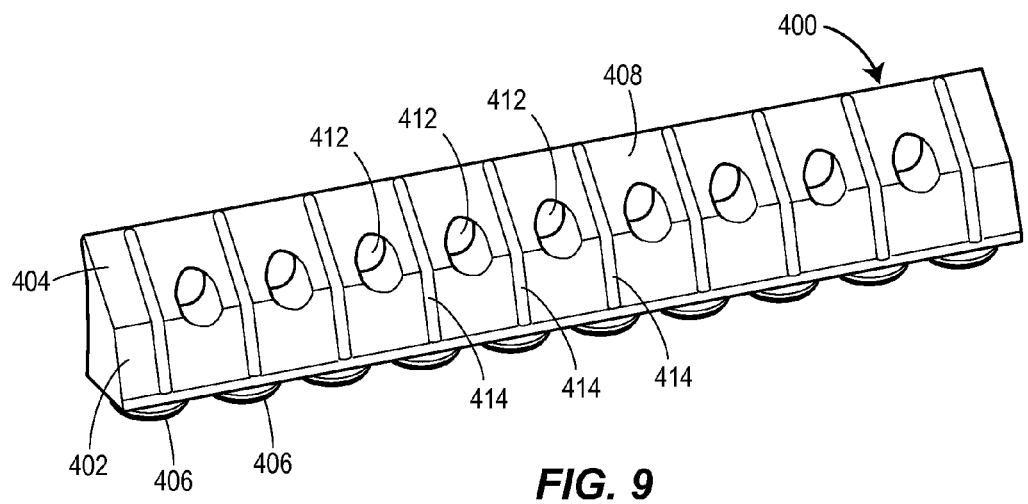
FIG. 9 is an isometric view of a configurable instrument retention member according to still a further aspect of the application.
Figure 9A:
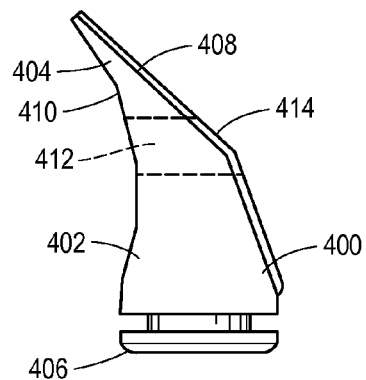
FIG. 9A is an end elevational view of the instrument retention member of FIG. 9.

FIGS. 9 and 9A show another configurable instrument retention member in the form of an instrument locating rail 400. The instrument locating rail 400 includes an elongate body 402 extending from a first end to a second end, a fin 404 projecting upwardly from a top of the body 402 and arranged to engage against a medical or dental instrument handle, and one or more connectors 406 disposed along a bottom of the body for connecting the instrument locating rail 400 to a sterilization cassette tray. Preferably, the instrument locating rail 400 is formed of a resilient flexible material, such as silicone rubber; however, the instrument locating rail 400 may be formed of rigid material, such as metal or rigid thermoplastic, and/or combinations thereof.

The fin 404 extends along the top of the body 402. Preferably, the fin 404 extends from the first end of the body 402 to the second end of the body 402 and forms a continuous surface for engagement against one or more medical or dental instruments. However, the fin 404 may in some arrangements only extend part way between the first and second ends of the body and/or have one or more separations, such as slits or recesses, disposed transversely through the fin to form a plurality of individual fins along the top of the body 402. The fin 404 has a slanted top surface 408 for engaging against the medical or dental instrument. Preferably, the fin 404 is resilient and flexes against the instrument. The fin 404 optionally is disposed at an angle from a plane perpendicular to the main wall of the cassette tray, such as between approximately 5 degrees and approximately 85 degrees from a vertical plane as viewed in the drawings, whereby a bottom side 410 of the fin 404 optionally projects laterally away from the body 402 at an angle such that the fin 404 is cantilevered at an angle laterally from the body 402.

One or more flow channels 412 are optionally disposed laterally through the body 402 and/or fin 404. The flow channels 412 may take any form, such as through bores, windows, slots or other type of opening, sufficient to allow steam and/or water to flow transversely through the instrument locating rail 400, which can increase the flow of steam and/or water through a sterilization cassette, for example, during a sterilization process in an autoclave. The flow channels 412 are preferably spaced apart longitudinally and disposed along the entire length of the body 402.

One or more lateral ridges 414 are optionally disposed on the top surface 408 of the fin 404. Preferably, the lateral ridges 414 are arranged to form transverse channels between the top surface 408 and a medical or dental instrument engaged against the top surface 408, wherein the channels allow steam and/or water to flow transversely between the top surface 408 and the instrument. The lateral ridges 414 are particularly useful for forming such lateral channels if the fin 404 is made of a flexible material that generally conforms to the shape of the instruments. The lateral ridges 414 may extend entirely from a top tip of the fin 404 to a bottom of the body 402 or may extend only along the top surface 408 of the fin 404, or may have other lengths sufficient to form the lateral channels as described above. In other arrangements, the lateral ridges 414 may be replaced by other shapes sufficient to form the lateral channels, such as raised knobs, fingers, and/or a randomly roughened surface, as long as the shapes allow water and/or steam to pass through the channels between the top surface 408 and an instrument.

The connectors 406 may take any form sufficient to allow the instrument locating rail 400 to be arranged in a plurality of different configurations in a sterilization cassette tray as described previously herein. For example, the connectors 406 may have the form of the connectors 72 or 72a as shown in the drawings to engage the openings 70 in the trays 32, 34 as described previously. Alternatively, connectors 406 may have the form of the flanges 314, 316 to engage opposing pairs of up-turned tabs 304 on the main wall 302 as described previously. Other forms of the connectors 406 may also be used.

As with previously described configurable instrument retention members, two or more of the instrument locating rail 400 may be used together or with any one or more of others of the instrument retention members disclosed herein to form an instrument retentions system in a sterilization cassette system.

Figure 10:
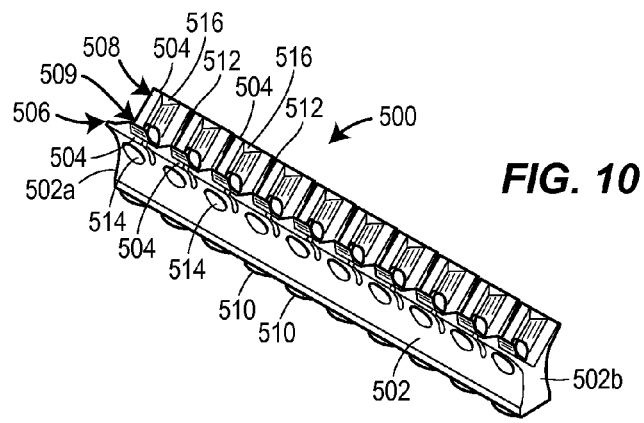
FIG. 10 is an isometric view of a configurable instrument retention member according to yet another aspect of the application.
Figure 10A:
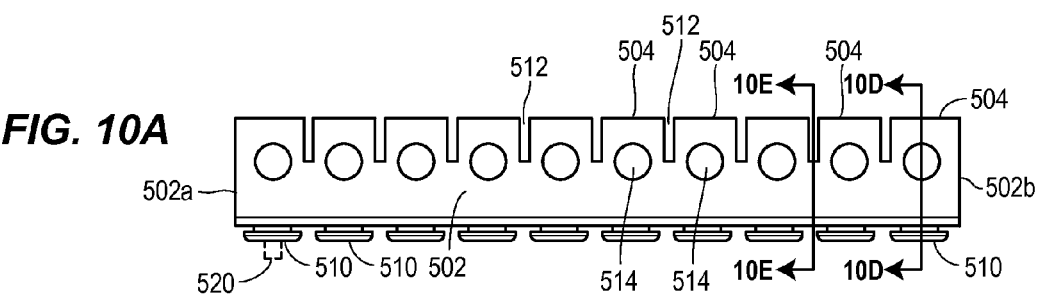
FIG. 10A is a side elevation view of the configurable instrument retention member of FIG. 10.
Figure 10B:
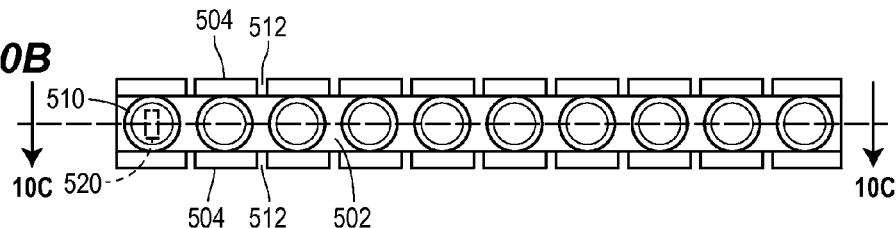
FIG. 10B is a bottom plan view of the configurable instrument retention member of FIG. 10.
Figure 10C:
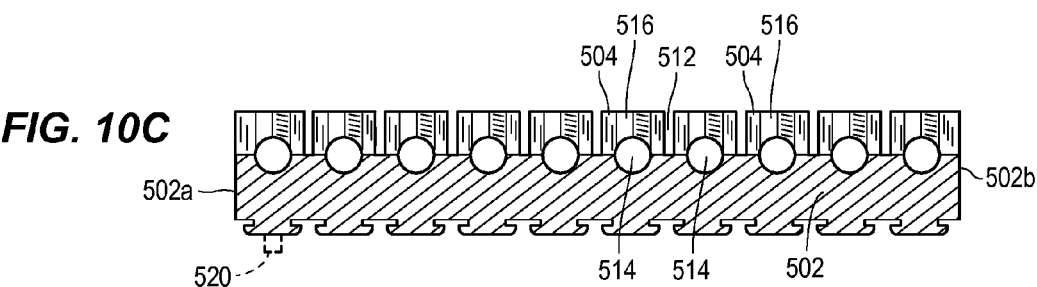
FIG. 10C is an axial cross-sectional view along the line C-C of FIG. 10A.
Figure 10D:
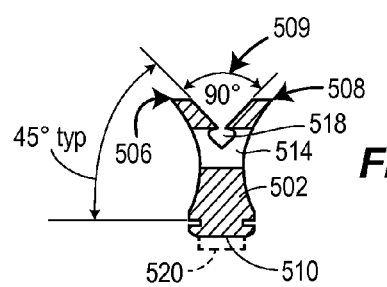
FIG. 10D is a lateral cross-sectional view along the line A-A of FIG. 10.
Figure 10E:
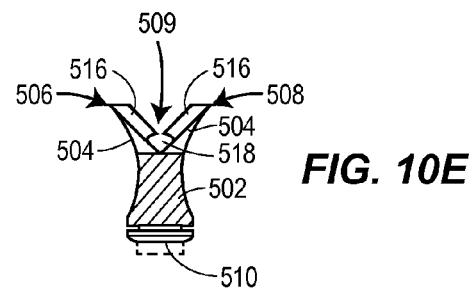
FIG. 10E is a lateral cross-sectional view along the line B-B of FIG. 10.

FIGS. 10-10E illustrate yet another configurable instrument retention member in the form of an instrument locating rail 500. The instrument locating rail 500 includes an elongate body 502 extending from a first end to a second end, a plurality of fins 504 projecting upwardly from a top of the body 502 and arranged in a first row 506 opposite a second row 508, and a plurality of connectors 510 disposed along a bottom of the body 502. The fins 504 of the first row 506 flare laterally apart from each other to form an axial channel 509, which is preferably generally V-shaped lateral profile, extending axially therebetween. Preferably, the instrument locating rail 500 is formed of a resilient flexible material, such as silicone rubber; however, the instrument locating rail 500 may be formed of rigid material, such as metal or rigid thermoplastic, and/or combinations thereof.

The instrument locating rail 500 may be used in a sterilization cassette system in opposing pairs, for example, with one instrument locating rail 500 attached to the main wall 36 and a second instrument locating rail 500 attached to the main wall 50 and aligned to be directly opposing each other such that the body 502 and fins 504 of one rail are aligned opposite the body 502 and fins 504 of the other rail.

The first row 506 of fins 504 extends longitudinally along the left side of the body 502 from the first end 502a to the second end 502b. The second row 508 of fins 504 extends longitudinally along the right side of the body 502 from the first end 502a to the second end 502b. The fins 504 in the first row 506 are angled away from the vertical centerline of the body 502 in a first lateral direction, such as at an angle between about 5° and about 85°, and preferably at an angle of approximately 45°. The fins 504 in the second row 508 are angled away from the vertical centerline center of the body 502 in a second lateral direction opposite the first lateral direction, such as at an angle between about 5° and about 85°, and preferably at an angle of approximately 45°. The first row 506 and the second row 508 are angled apart from each other to form an included angle between opposing fins 504 of approximately 90°, although in other arrangements, other included angles may be formed between 0° and 180°. The fins 504 in each row 506 and 508 are axially aligned, preferably parallel with the longitudinal axis of the body 502.

In each row 506 and 508, adjacent fins 504 are separated axially from each other, such as with a gap 512 or a slit. Preferably, each fin 504 has the same dimensions and each gap 512 has the same dimensions, such that each row 506 and 508 is formed of a regularly repeating series of fins 504 separated by gaps 512. Each fin 504 in the first row 506 is laterally aligned opposite a corresponding fin 504 in the second row 508. Each gap 512 in the first row 506 is laterally aligned opposite a corresponding gap 512 in the second row 508. This axial separation allows the individual fins 504 to flex independently of the adjacent fins 504, such that an instrument pressed laterally across a first set of fins 504 does not deform the next adjacent set of fins 504. In this way, the instrument locating rail 500 can accommodate multiple tools disposed laterally across the top surfaces of the fins 504 axially spaced apart along the tops of the fins 504, and can receive different diameter tools, without the tools falling or bunching together axially along the body 502, and without larger diameter tool handles adversely influencing the ability of opposing rails to securely support smaller diameter handles located on adjacent fins 504 axially along the V-shaped channel. In some arrangements, the ability of the fins 504 to flex completely independently of each other also ensure more thorough flow of disinfecting fluid around the entire surface of each of the tools because spaces can be maintained between adjacent tools.

One or more flow channels 514 extend laterally through the instrument locating rail 500, for example, to allow the passage of steam and/or other disinfecting fluid through the instrument locating rail. Each flow channel 514 is aligned with a pair of opposing fins 504 in the first and second rows 506, 508. Each flow channel extends laterally through the body, and preferably, through a lower portion of the respective pair of opposing fins 504, forming a through bore from one side of the instrument locating rail 500 to the opposite side.

A ridge 516 is disposed on the inner/upper surface of each fin 504 and extends vertically, such as from a top end of the fin 504 toward a bottom end of the fin 504. Preferably, each of the ridges 516 is substantially identical, and so only a single ridge is described for ease of understanding. The ridge 516 is vertically aligned with a corresponding flow channel 514. A bottom end of the ridge 516 ends at the corresponding flow channel 514. The ridge 516 preferably has an elongate triangular shape profile extending from its top end to its bottom end. The side edges of the ridge are spaced axially inwardly from the adjacent side edges of the fin 504, for example, forming a flat strip of the surface of the fin adjacent each side edge of the fin.

The connectors 510 are spaced apart axially along the bottom side of the body 502. The connectors 510 are disposed in a row extending substantially from the first end 502a to the second end 502b. Each connector 510 is substantially identical to the connectors 406, including a circular head disposed on a narrow neck and spaced apart from the bottom surface of the body 502; although other types of connectors, such as any of the connectors disclosed herein, may be used in different arrangements. The head of the connector 510 is sized to be press fit through a hole 70 and to slightly overhang at least a portion of the hole 70 to lockingly engage the perimeter of the hole after being press fit through the hole. In one such arrangement, at least one width dimension of the head, such as a diameter, is slightly larger than a corresponding width dimension of the hole 70. The connectors 510 are sized and spaced apart so as to be insertable into the openings 70 of the main walls 50 and/or 36 of a the trays 32 and/or 34 in a plurality of different arrangements and alignments. A connector 510 is axially aligned with each opposing pair of fins 504 and a flow passage 514, preferably along a centerline of the ridges 516 on the opposing pair of fins 504.

Optionally, one or more of the connectors 510 may include a small projection 520, such as a small tab, arranged to allow a user to pull the connector through a hole 70 in the cassette trays 32, 34, for example with pliers, such as needle nose pliers, or a similar tool. the projection may be rectangular, cylindrical, or another shape easily gripped by a pair of needle nosed pliers and suitable for pulling the head of the connector through the hole 70. Furthermore, since the small projection 520 only serves to facilitate insertion of the connectors 510 through the holes 70 of the cassette trays 32, 34, the projection 520 may be cut away or otherwise removed from the exposed surface of the connectors 510 after installation of the instrument locating rail 500, if desired. Since the projections 520 could be so removed, they are illustrated in dashed lines. In some arrangements, the projection 520 is sized and shaped to be easily grasped between the fingers of a person to pull the connector 510 through the hole 70.

As best seen in FIGS. 10D and 10E, a smaller axial channel 518 extends along the bottom of the V-shaped channel 509, between the bottom ends of the ridges 516 and the intersection of the first row 506 of fins 504 and the second row 508 of fins 504. The axial channel 518 extends along the top of the body 502 from the first end 502a to the second end 502b. The axial channel 518 in some arrangements and uses forms an axial pathway for steam and/or other disinfecting fluid to flow axially past tools carried on the fins 504, thereby allowing for improved flow of disinfecting fluid around the surface of the tools.

The instrument locating rail 500 may have any reasonable combination of sizes and dimensions. In one arrangement, for example, the body 502 is 5 inches long from the first end 502a to the second end 502b; the rail has a total height of ¾ inches from the bottom of the connectors 520 to the top of the fins 504; each flow channel 514 has a diameter of ¼ inch and is spaced 0.45 inches on center up from the bottom surface of the body 502; each connector 510 has a diameter of 0.4 inches; the body 502 has a lateral width of 0.4 inches at the bottom surface and the fins 504 may have a lateral width of 0.64 inches across the top ends thereof; each fin 504 has an axial length of 0.47 inches; each axially aligned set of opposing fins 504, flow channel 514, and connector 510 is spaced axially at ½ inch on center such that each gap 512 has an axial width of 0.06 inches; the head of each connector 510 is spaced 0.04 inches from the bottom side of the body 502; and each ridge 516 has a apex height of 0.07 inches. These dimensions are only exemplary and are not to be considered as limiting. The right to other sizes and dimensions is expressly reserved.

Figure 10F:
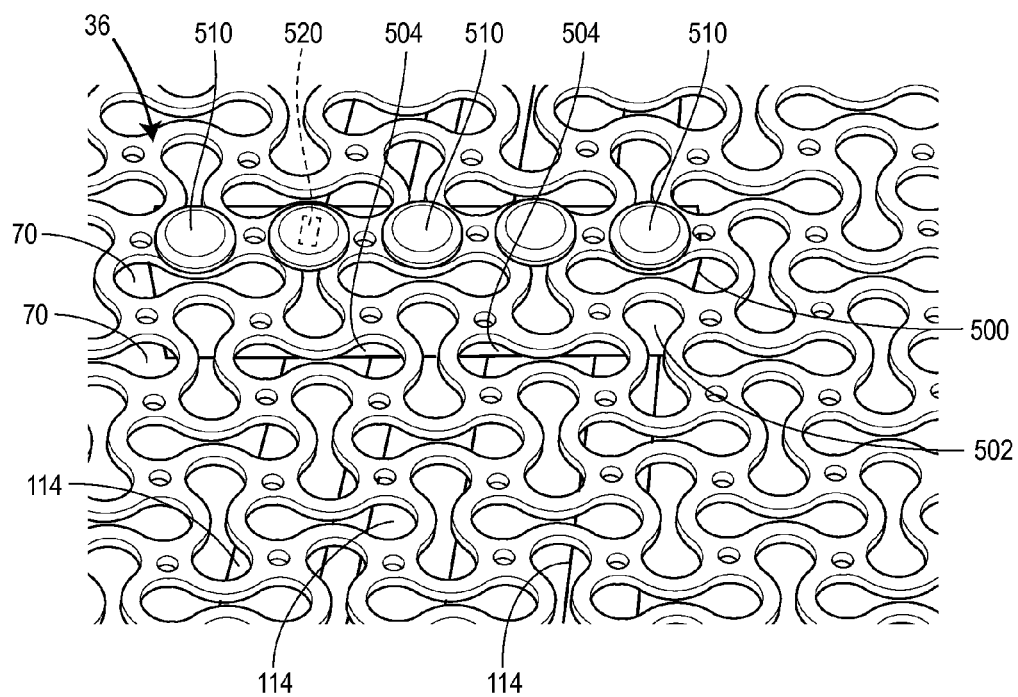
FIG. 10F is an enlarged perspective partial view of the configurable instrument retention member of FIG. 10 secured to a main wall of a cassette.

FIG. 10F illustrates the instrument locating rail 500 attached to the main wall 36 of the cassette tray 32, for example. The holes 70 are formed in hourglass shaped pairs, for example, defined by a figure-8 shaped outline in the main wall 36. The heads of the connectors 510 are fit, such as by press fitting, through a row of holes 70. The heads of the connectors 510 lock the instrument locating rail 500 to the main wall 36. A plurality of instrument handles 114 is illustrated clamped against the instrument locating rail 500.

As with previously described configurable instrument retention members, two or more of the instrument locating rail 500 may be used together or with any one or more of others of the instrument retention members disclosed herein to form an instrument retentions system in a sterilization cassette system.

INDUSTRIAL APPLICABILITY

The sterilization cassette systems, instrument retention systems, and configurable instrument retention members disclosed herein are useful for sterilizing and/or storing medical and/or dental instruments. Other utilities are also possible.

Numerous modifications to the present invention will be apparent to those skilled in the art in view of the foregoing description. Accordingly, this description is to be construed as illustrative only and is presented for the purpose of enabling those skilled in the art to make and use the sterilization and storage cassette systems and components and to teach the best mode of carrying out same.

We claim:

1. A configurable instrument retention member for use with a sterilization cassette tray, the configurable instrument retention member comprising:

an elongate body extending from a first end to a second end;

a first row of fins projecting upwardly from a top of the elongate body, each of the fins of the first row of fins having a ridge disposed on an upper inner surface thereof;

a second row of fins projecting upwardly from the top of the body, each of the fins of the second row of fins having a ridge disposed on an upper inner surface thereof, the first row of fins and the second row of fins forming a channel therebetween, each of the fins of the second row of fins aligned with a corresponding one of the fins of the first row of fins;

a plurality of flow channels extending through the elongate body, each of the flow channels aligned with a corresponding one of the fins of the first row of fins and one of the fins of the second row of fins; and one or more connectors for connecting an instrument locating rail to a sterilization cassette tray disposed along a bottom of the elongate body; and wherein the fins in at least one of the first and second rows of fins are spaced apart, defining a gap between adjacent pairs of fins in the row.

2. The configurable instrument retention member of claim 1, wherein the channel has a V-shaped profile.

3. The configurable instrument retention member of claim 1, each of the plurality of flow channels extending through one of the fins of each of the first and second rows of fins.

4. The configurable instrument retention member of claim 1, each of the ridges being vertically aligned with a corresponding one of the plurality of flow channels.

5. The configurable instrument retention member of claim 4, wherein each of the ridges extends from a top edge of each of the fins of the first and second rows of fins to the corresponding one of the plurality of flow channels.

6. The configurable instrument retention member of claim 4, wherein each ridge allows fluid to flow between the upper inner surface of the corresponding fin and an instrument pressed against the upper inner surface.

7. The configurable instrument retention member of claim 1, further comprising:

a tab for being grasped by a pair of pliers disposed on a bottom surface of one or more of the connectors.

8. The configurable instrument retention member of claim 1, each of the ridges being triangular in cross-section, tapering inwardly from a widest end at a surface of the fin from which the ridge projects opposite an aligned fin of the other row of fins, to a narrowest point closest to the aligned fin of the other row of fins.

* * * * *